(12) United States Patent
Parikh et al.

(10) Patent No.: US 12,370,308 B2
(45) Date of Patent: *Jul. 29, 2025

(54) DETERMINATION OF ADJUSTMENTS TO FLUID DELIVERY SETTINGS

(71) Applicant: MEDTRONIC MINIMED, INC., Northridge, CA (US)

(72) Inventors: Neha J. Parikh, West Hills, CA (US); Anirban Roy, Agoura Hills, CA (US); Benyamin Grosman, Winnetka, CA (US); Patrick E. Weydt, Moorpark, CA (US); Louis J. Lintereur, Boise, ID (US); Di Wu, Palo Alto, CA (US); Francine R. Kaufman, Los Angeles, CA (US); Scott W. Lee, Redlands, CA (US)

(73) Assignee: MEDTRONIC MINIMED, INC., Northridge (CA)

(*) Notice: Subject to any disclaimer, the term of this patent is extended or adjusted under 35 U.S.C. 154(b) by 227 days.

This patent is subject to a terminal disclaimer.

(21) Appl. No.: 17/504,568

(22) Filed: Oct. 19, 2021

(65) Prior Publication Data
US 2022/0031946 A1    Feb. 3, 2022

Related U.S. Application Data

(63) Continuation of application No. 15/960,495, filed on Apr. 23, 2018, now Pat. No. 11,147,919.

(51) Int. Cl.
*A61M 5/172* (2006.01)
*G16H 20/17* (2018.01)
*A61M 5/142* (2006.01)

(52) U.S. Cl.
CPC .......... *A61M 5/1723* (2013.01); *A61M 5/172* (2013.01); *G16H 20/17* (2018.01);
(Continued)

(58) Field of Classification Search
None
See application file for complete search history.

(56) References Cited

U.S. PATENT DOCUMENTS

| 4,562,751 A | 1/1986 | Nason et al. |
| 4,685,903 A | 8/1987 | Cable et al. |

(Continued)

FOREIGN PATENT DOCUMENTS

| AU | 2019260574 A1 | 10/2020 |
| CA | 3107454 A1 | 10/2019 |

(Continued)

OTHER PUBLICATIONS

Davidson PC, Hebblewhite HR, Steed RD, Bode BW. Analysis of guidelines for basal-bolus insulin dosing: basal insulin, correction factor, and carbohydrate-to-insulin ratio. Endocr Pract. Dec. 2008;14(9):1095-101. doi: 10.4158/EP.14.9.1095. PMID: 19158048. (Year: 2008).*

(Continued)

*Primary Examiner* — Jenna Zhang
(74) *Attorney, Agent, or Firm* — Weaver Austin Villeneuve & Sampson LLP

(57) ABSTRACT

Disclosed herein are techniques related to determination of adjustments to fluid delivery settings. In some embodiments, the techniques may involve accessing insulin delivery data for a user of an insulin delivery device. The insulin delivery data may be indicative of an amount of insulin delivered by the insulin delivery device to the user during a time period. The techniques may also involve analyzing the insulin delivery data to generate an updated insulin sensitivity factor (ISF) value. The techniques may further involve generating, based on the updated ISF value, a recommendation to adjust an ISF value of the insulin delivery device. Additionally, the techniques may involve causing adjustment of the ISF value
(Continued)

to the updated ISF value in accordance with the recommendation.

20 Claims, 3 Drawing Sheets

(52) U.S. Cl.
CPC .............. *A61M 2005/14208* (2013.01); *A61M 2205/50* (2013.01); *A61M 2205/502* (2013.01); *A61M 2230/201* (2013.01)

(56) References Cited

U.S. PATENT DOCUMENTS

| | | | |
|---|---|---|---|
| 4,755,173 A | 7/1988 | Konopka et al. | |
| 5,080,653 A | 1/1992 | Voss et al. | |
| 5,097,122 A | 3/1992 | Colman et al. | |
| 5,391,250 A | 2/1995 | Cheney, II et al. | |
| 5,485,408 A | 1/1996 | Blomquist | |
| 5,505,709 A | 4/1996 | Funderburk et al. | |
| 5,522,803 A | 6/1996 | Teissen-Simony | |
| 5,665,065 A | 9/1997 | Colman et al. | |
| 5,800,420 A | 9/1998 | Gross et al. | |
| 5,807,375 A | 9/1998 | Gross et al. | |
| 5,925,021 A | 7/1999 | Castellano et al. | |
| 5,954,643 A | 9/1999 | Antwerp et al. | |
| 6,017,328 A | 1/2000 | Fischell et al. | |
| 6,088,608 A | 7/2000 | Schulman et al. | |
| 6,119,028 A | 9/2000 | Schulman et al. | |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,485,465 B2 | 11/2002 | Moberg et al. | |
| 6,544,212 B2 | 4/2003 | Galley et al. | |
| 6,554,798 B1 | 4/2003 | Mann et al. | |
| 6,558,320 B1 | 5/2003 | Causey, III et al. | |
| 6,558,351 B1 | 5/2003 | Steil et al. | |
| 6,589,229 B1 | 7/2003 | Connelly et al. | |
| 6,591,876 B2 | 7/2003 | Safabash | |
| 6,641,533 B2 | 11/2003 | Causey, III et al. | |
| 6,659,980 B2 | 12/2003 | Moberg et al. | |
| 6,736,797 B1 | 5/2004 | Larsen et al. | |
| 6,740,072 B2 | 5/2004 | Starkweather et al. | |
| 6,749,587 B2 | 6/2004 | Flaherty | |
| 6,752,787 B1 | 6/2004 | Causey, III et al. | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 6,817,990 B2 | 11/2004 | Yap et al. | |
| 6,827,702 B2 | 12/2004 | Lebel et al. | |
| 6,932,584 B2 | 8/2005 | Gray et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,323,142 B2 | 1/2008 | Pendo et al. | |
| 7,399,277 B2 | 7/2008 | Saidara et al. | |
| 7,402,153 B2 | 7/2008 | Steil et al. | |
| 7,442,186 B2 | 10/2008 | Blomquist | |
| 7,602,310 B2 | 10/2009 | Mann et al. | |
| 7,621,893 B2 | 11/2009 | Moberg et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Nunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2 | 11/2012 | Hanson et al. | |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 8,474,332 B2 | 7/2013 | Bente, IV et al. | |
| 8,674,288 B2 | 3/2014 | Hanson et al. | |
| 9,526,834 B2 | 12/2016 | Keenan et al. | |
| 9,907,909 B2 | 3/2018 | Finan et al. | |
| 11,147,919 B2 | 10/2021 | Parikh et al. | |
| 11,158,413 B2 | 10/2021 | Grosman et al. | |
| 11,367,526 B2 | 6/2022 | Chiu et al. | |
| 11,986,629 B2 | 5/2024 | Wu et al. | |
| 12,073,932 B2 | 8/2024 | Grosman et al. | |
| 2002/0193679 A1* | 12/2002 | Malave | A61M 5/172 600/407 |
| 2007/0123819 A1 | 5/2007 | Mernoe et al. | |
| 2008/0262745 A1 | 10/2008 | Polidori | |
| 2008/0269714 A1* | 10/2008 | Mastrototaro | A61B 5/14865 604/504 |
| 2009/0036753 A1* | 2/2009 | King | A61B 5/4839 600/301 |
| 2009/0164239 A1 | 6/2009 | Hayter et al. | |
| 2010/0160861 A1 | 6/2010 | Causey, III et al. | |
| 2010/0249561 A1 | 9/2010 | Patek et al. | |
| 2011/0130746 A1 | 6/2011 | Budiman | |
| 2011/0208156 A1 | 8/2011 | Doyle, III et al. | |
| 2013/0030358 A1* | 1/2013 | Yodfat | A61M 5/14248 702/19 |
| 2013/0190583 A1 | 7/2013 | Grosman et al. | |
| 2013/0231642 A1 | 9/2013 | Doyle, III et al. | |
| 2013/0338630 A1 | 12/2013 | Agrawal et al. | |
| 2014/0066889 A1 | 3/2014 | Grosman et al. | |
| 2014/0066892 A1* | 3/2014 | Keenan | A61B 5/14532 604/506 |
| 2014/0128705 A1 | 5/2014 | Mazlish | |
| 2014/0200559 A1 | 7/2014 | Doyle, III et al. | |
| 2014/0276554 A1 | 9/2014 | Finan et al. | |
| 2014/0276555 A1 | 9/2014 | Morales | |
| 2015/0057807 A1 | 2/2015 | Mastrototaro et al. | |
| 2015/0352282 A1* | 12/2015 | Mazlish | G16H 40/63 |
| 2016/0030339 A1 | 2/2016 | Muhlen-Bartmer et al. | |
| 2016/0162662 A1* | 6/2016 | Monirabbasi | G16H 10/40 604/504 |
| 2017/0056591 A1 | 3/2017 | Breton et al. | |
| 2017/0143899 A1 | 5/2017 | Gondhalekar et al. | |
| 2017/0189614 A1* | 7/2017 | Mazlish | A61M 5/1407 |
| 2017/0332952 A1 | 11/2017 | Desborough et al. | |

(56) References Cited

U.S. PATENT DOCUMENTS

| | | |
|---|---|---|
| 2018/0020988 A1 | 1/2018 | Patek |
| 2018/0099092 A1 | 4/2018 | Roy |
| 2018/0174675 A1 | 6/2018 | Roy et al. |
| 2018/0200439 A1* | 7/2018 | Mazlish ............... A61M 5/1723 |
| 2018/0200441 A1 | 7/2018 | Desborough et al. |
| 2018/0286518 A1 | 10/2018 | Raju et al. |
| 2018/0296757 A1* | 10/2018 | Finan .................... G16H 20/17 |
| 2019/0005195 A1 | 1/2019 | Peterson et al. |
| 2019/0258904 A1 | 8/2019 | Ma et al. |
| 2019/0336684 A1 | 11/2019 | O'Connor et al. |
| 2020/0093988 A1 | 3/2020 | Zhong et al. |
| 2020/0098463 A1 | 3/2020 | Arunachalam et al. |
| 2020/0098464 A1 | 3/2020 | Velado et al. |
| 2020/0098465 A1 | 3/2020 | Jiang et al. |
| 2020/0101221 A1 | 4/2020 | Lintereur et al. |
| 2020/0101224 A1 | 4/2020 | Lintereur et al. |
| 2020/0135311 A1 | 4/2020 | Mairs |
| 2020/0246543 A1 | 8/2020 | Sadeghzadeh et al. |
| 2020/0282141 A1 | 9/2020 | Rousson et al. |
| 2020/0342974 A1 | 10/2020 | Chen et al. |
| 2020/0390973 A1 | 12/2020 | Wu et al. |
| 2021/0100486 A1 | 4/2021 | Romero Ugalde et al. |
| 2022/0044785 A1 | 2/2022 | Grosman et al. |
| 2024/0261505 A1 | 8/2024 | Wu et al. |
| 2024/0371492 A1 | 11/2024 | Grosman et al. |

FOREIGN PATENT DOCUMENTS

| | | |
|---|---|---|
| CN | 104520862 A | 4/2015 |
| CN | 104756116 A | 7/2015 |
| CN | 104769595 A | 7/2015 |
| CN | 112005310 A | 11/2020 |
| CN | 113646847 A | 11/2021 |
| EP | 3785276 A1 | 3/2021 |
| EP | 3935646 A1 | 1/2022 |
| JP | 2003079723 A | 3/2003 |
| JP | 2005508025 A | 3/2005 |
| JP | 2008545493 A | 12/2008 |
| JP | 2010523167 A | 7/2010 |
| JP | 2010532044 A | 9/2010 |
| JP | 2011523940 A | 8/2011 |
| JP | 2021522582 A | 8/2021 |
| KR | 20210004993 A | 1/2021 |
| WO | 2014035570 A2 | 3/2014 |
| WO | 2014035672 A2 | 3/2014 |
| WO | 2016133879 A1 | 8/2016 |
| WO | 2018033513 A1 | 2/2018 |
| WO | 2019209602 A1 | 10/2019 |
| WO | 2020214780 A1 | 10/2020 |

OTHER PUBLICATIONS

CN Office Action dated Oct. 12, 2023 in CN Application No. CN201980025847.6 with English translation.
Hughes, C., et al., Safety Supervision System Design and Implications for Continuous Subcutaneous Insulin Infusion (Csii) In T1DM, Ph.D. Dissertation, University of Virginia, 2011, 240 pages.
International Preliminary Report on Patentability dated Oct. 28, 2021, in PCT Application No. PCT/US2020/028461.
International Search Report and Written Opinion dated Jul. 9, 2020, in Application No. PCT/US2020/028461.
JP Office Action dated Mar. 14, 2023 in Application No. JP2020-559417 with English translation.
Kirchsteiger, H., et al., "Reduced Hypoglycemia Risk in Insulin Bolus Therapy Using Asymmetric Cost Functions," Proceedings of the 7th Asian Control Conference, Aug. 2009, pp. 751-756.
U.S. Advisory Action dated Dec. 12, 2023 in U.S. Appl. No. 16/438,407.
U.S Advisory Action dated Jun. 20, 2023 in U.S. Appl. No. 16/438,407.
U.S Advisory Action dated Sep. 16, 2022 in U.S. Appl. No. 16/438,407.
U.S. Final Office Action dated Apr. 4, 2023 in U.S. Appl. No. 16/438,407.
U.S. Final Office Action dated Jul. 5, 2022 in U.S. Appl. No. 16/438,407.
U.S. Final Office Action dated Oct. 24, 2023 in U.S. Appl. No. 16/438,407.
U.S. Non-Final Office Action dated Dec. 23, 2022 in U.S. Appl. No. 16/438,407.
U.S. Non-Final Office Action dated Jan. 21, 2021, in U.S. Appl. No. 15/960,495.
U.S. Non-Final Office Action dated Jul. 19, 2023, in U.S. Appl. No. 16/438,407.
U.S. Non-Final Office Action dated Mar. 14, 2022 in U.S. Appl. No. 16/438,407.
U.S. Non-Final Office Action dated Mar. 31, 2021, in U.S. Appl. No. 16/386,104.
U.S. Non-Final Office Action dated Oct. 6, 2023, in U.S. Appl. No. 17/509,670.
Wang, Q et al., "Model Predictive Control for Type 1 Diabetes Based on Personalized Linear Time-Varying Subject Model Consisting of both Insulin and Meal Inputs: in Silica Evaluation", American Control Conference, Jul. 2015, Chicago, IL, USA, pp. 5782-5787.
Zarkogianni, K., et al., "An Insulin Infusion Advisory System Based on Autotuning Nonlinear Model-Predictive Control," IEEE Transactions on Biomedical Engineering, 2011, vol. 55 (9), pp. 2467-2477.
AU Office Action dated Oct. 31, 2023 in AU Application No. 2019260574 [MEDTP030].
Lee, et al., "Thesis: Personalization and Enhanced Designs for Automated Glucose Control in Artificial Pancreas," University of California Santa Barbara, 2016, pp. 1-152.
U.S. Notice of Allowance dated Apr. 16, 2024 in U.S. Appl. No. 17/509,670 [MEDTP031X1C1US].
U.S. Notice of Allowance dated Apr. 24, 2024 in U.S. Appl. No. 17/509,670 [MEDTP031X1C1US].
U.S. Notice of Allowance dated Jan. 31, 2024 in U.S. Appl. No. 16/438,407 [MEDTP014US].
U.S. Appl. No. 18/639,434, inventors Wu D, et al., filed on Apr. 18, 2024 [MEDTP014C1US].
Zavitsanou, et al., "Embedded Control in Wearable Medical Devices: Application to the Artificial Pancreas," ProQuest, 2016, vol. 4(35), pp. 1-29.
CN Office Action dated Oct. 25, 2024 in CN Application No. 202080027737.6 with English translation [MEDTP014].
EP Office Action dated Jun. 26, 2024 in EP Application No. 20724639.8 [MEDTP014].

* cited by examiner

DETERMINATION OF ADJUSTMENTS TO FLUID DELIVERY SETTINGS

CROSS-REFERENCE TO RELATED APPLICATIONS

The present application is a Continuation Application claiming the benefit of and priority to U.S. patent application Ser. No. 15/960,495, filed on Apr. 23, 2018, now U.S. Pat. No. 11,147,919, the entire disclosure of which is incorporated by reference herein.

TECHNICAL FIELD

Embodiments of the disclosed subject matter are directed to systems and methods for diabetes therapy management. More specifically, embodiments of the disclosed subject matter are directed to systems and methods that analyze data associated with the operation of a medication fluid infusion device, for purposes of generating and implementing recommendations that adjust certain settings of the infusion device.

BACKGROUND

The pancreas of a normal healthy person produces and releases insulin into the blood stream in response to elevated blood plasma glucose levels. Beta cells (β-cells), which reside in the pancreas, produce and secrete the insulin into the blood stream, as it is needed. If β-cells become incapacitated or die, a condition known as Type I diabetes mellitus (or in some cases if β-cells produce insufficient quantities of insulin, Type II diabetes), then insulin must be provided to the body from another source. Diabetes affects approximately eight percent of the total population in the United States alone.

Traditionally, because insulin cannot be taken orally, it has been injected with a syringe. However, use of infusion pump therapy has been increasing, especially for delivering insulin for diabetics. For example, external infusion pumps are worn on a belt, in a pocket, or the like, and deliver insulin into the body via an infusion tube with a percutaneous needle or a cannula placed in the subcutaneous tissue. Physicians have recognized that continuous infusion provides greater control of a diabetic's condition, and are also increasingly prescribing it for patients.

Patient-related and pump-related data can be collected during operation of an insulin infusion pump, for subsequent review and analysis. For example, glucose sensor data, insulin delivery data, and/or other data generated or collected by the infusion pump can be analyzed in an appropriate manner to determine whether or not it might be desirable to recommend changes to one or more settings of the infusion device. Accordingly, various settings of the infusion device can be adjusted in a patient-specific manner to improve and optimize the patient's therapy (in accordance with the analyzed data).

BRIEF SUMMARY

Disclosed herein are techniques related to determination of adjustments to fluid delivery settings. The techniques may be practiced using a processor-implemented method; a system comprising one or more processors and one or more processor-readable storage media; and one or more non-transitory processor-readable storage media.

In various embodiments, the techniques may involve accessing insulin delivery data for a user of an insulin delivery device. The insulin delivery data may be indicative of an amount of insulin delivered by the insulin delivery device to the user during a time period. The techniques may also involve analyzing the insulin delivery data to generate an updated insulin sensitivity factor (ISF) value. The techniques may further involve generating, based on the updated ISF value, a recommendation to adjust an ISF value of the insulin delivery device. Additionally, the techniques may involve causing adjustment of the ISF value to the updated ISF value in accordance with the recommendation.

BRIEF DESCRIPTION OF THE DRAWINGS

A more complete understanding of the subject matter may be derived by referring to the detailed description and claims when considered in conjunction with the following figures, wherein like reference numbers refer to similar elements throughout the figures.

DETAILED DESCRIPTION

Figure 1:
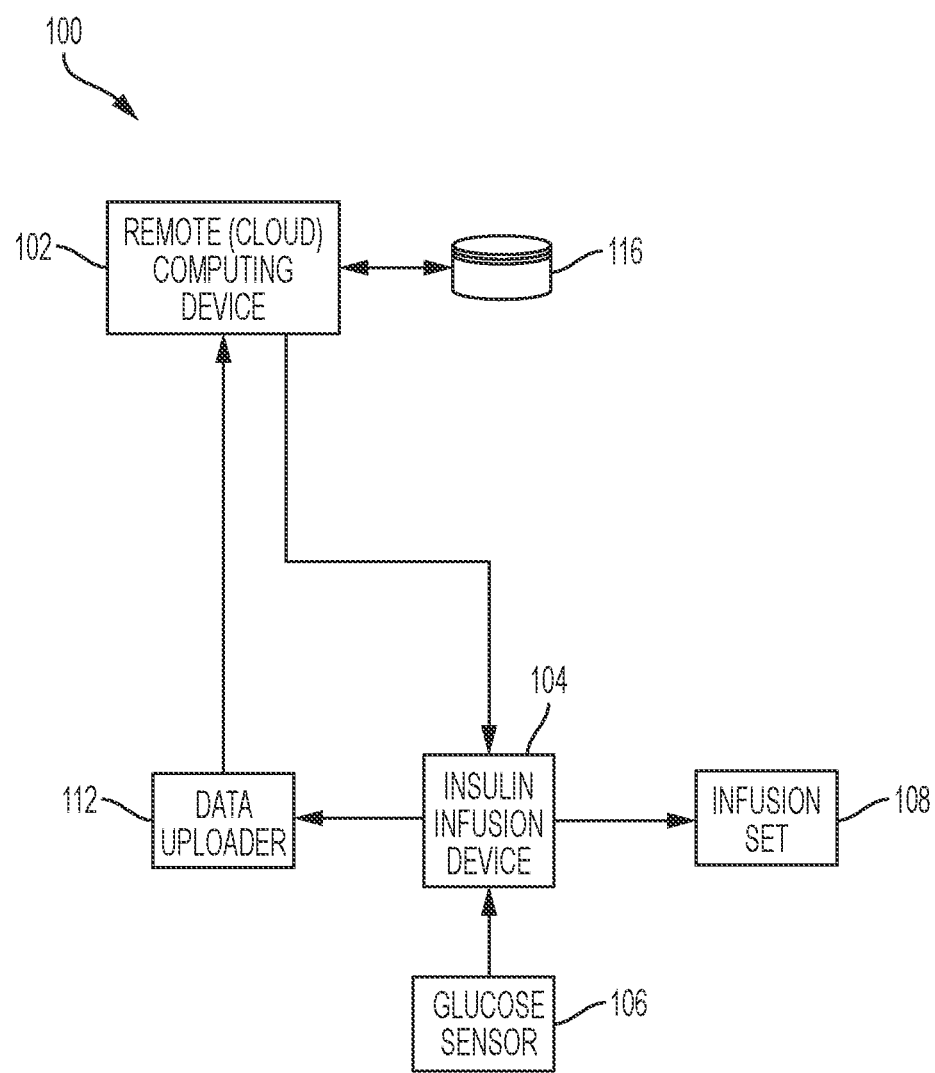
FIG. 1 is a simplified block diagram representation of an insulin infusion and management system that is configured and arranged in accordance with an exemplary embodiment of the invention.

The following detailed description is merely illustrative in nature and is not intended to limit the embodiments of the subject matter or the application and uses of such embodiments. As used herein, the word "exemplary" means "serving as an example, instance, or illustration." Any implementation described herein as exemplary is not necessarily to be construed as preferred or advantageous over other implementations. Furthermore, there is no intention to be bound by any expressed or implied theory presented in the preceding technical field, background, brief summary or the following detailed description.

Techniques and technologies may be described herein in terms of functional and/or logical block components, and with reference to symbolic representations of operations, processing tasks, and functions that may be performed by various computing components or devices. Such operations, tasks, and functions are sometimes referred to as being computer-executed, computerized, software-implemented, or computer-implemented. It should be appreciated that the various block components shown in the figures may be realized by any number of hardware, software, and/or firmware components configured to perform the specified functions. For example, an embodiment of a system or a component may employ various integrated circuit components, e.g., memory elements, digital signal processing elements, logic elements, look-up tables, or the like, which may carry out a variety of functions under the control of one or more microprocessors or other control devices.

When implemented in software, firmware, or processor-readable instructions, various elements of the systems described herein are essentially the code segments or instructions that perform the various tasks. In certain embodiments, the program or code segments are stored in a tangible processor-readable medium, which may include any medium that can store or transfer information. Examples of a non-transitory and processor-readable medium include an electronic circuit, a semiconductor memory device, a ROM, a flash memory, an erasable ROM (EROM), a floppy diskette, a CD-ROM, an optical disk, a hard disk, or the like.

The following description relates to a diabetes patient management system that generates and delivers recommendations for adjusting certain settings of an insulin infusion device used by the patient. The exemplary embodiment disclosed herein employs a cloud-based architecture, wherein most of the processor-intensive tasks are performed by one or more server systems that communicate with other devices in the system, e.g., a mobile client device, a portable insulin infusion device, a source of data (such as patient-related data, insulin pump data, and the like), and possibly other remote devices. The disclosed system obtains and processes patient-specific data, which is collected during operation of the patient's insulin infusion device in an automated closed-loop mode, to generate and implement recommended adjustments to certain settings of the insulin infusion device. The adjustments are applied during operation of the insulin infusion device in a manual delivery mode.

For the sake of brevity, conventional features and functionality related to infusion systems, insulin pumps, and infusion sets may not be described in detail here. Examples of infusion pumps and/or related systems used to administer insulin and other medications may be of the type described in, but not limited to, U.S. Pat. Nos. 5,505,709; 6,485,465; 6,554,798; 6,558,351; 6,659,980; 6,752,787; 6,817,990; 6,932,584; and 7,621,893; which are herein incorporated by reference. Moreover, United States patent application publication number US 2013/0338630 includes a description of a diabetes therapy management system for recommending adjustments to an insulin infusion device. Some features and functionality described therein can be leveraged by the system disclosed here. Accordingly, the disclosure of US 2013/0338630 is also incorporated by reference herein.

Turning now to the drawings, FIG. 1 is a simplified block diagram representation of an exemplary embodiment of an insulin infusion and management system 100 that is suitably configured to support the techniques and methodologies described in more detail below. The system 100 supports users of insulin infusion devices (patients, caregivers, healthcare providers, parents, etc.), and performs various techniques and methods to manage and control the use of insulin infusion devices. It should be appreciated that FIG. 1 depicts one possible implementation of the system 100, and that other arrangements, architectures, and deployments can be provided if so desired. The system 100 (which has been simplified for purposes of illustration) generally includes or cooperates with the following components, without limitation: a remote or "cloud" based computing device 102; an insulin infusion device 104; a continuous glucose sensor 106; and an infusion set 108 for the user/patient. The insulin infusion device 104, the glucose sensor 106, and the infusion set 108 are components of an insulin infusion system that is used by the patient to treat diabetes. The system 100 may also include or cooperate with an optional data uploader component 112.

At least some of the components of the system 100 are communicatively coupled with one another to support data communication as needed. For this particular example, the computing device 102 and the insulin infusion device 104 communicate with each other via a suitable data communication network (which is not depicted in FIG. 1). Moreover, the data uploader component 112 is preferably configured as an interface component that communicates data from the insulin infusion device 104 to the computing device 102 using a suitable data communication network. In certain embodiments, the insulin infusion device 104 and/or the continuous glucose sensor 106 are communicatively coupled to the network to facilitate the uploading of relevant data directly to the remote computing device 102. Alternatively, or additionally, the insulin infusion device 104 provides relevant data directly to the data uploader component 112, which in turn uploads the data to the remote computing device 102 via the network. Other configurations and topologies are also contemplated here, such as a system that includes one or more intermediary, interface, or data repeating devices in the data path between the computing device 102 and the infusion device 104.

FIG. 1 depicts network communication links in a simplified manner. In practice, the system 100 may cooperate with and leverage any number of wireless and any number of wired data communication networks maintained or operated by various entities and providers. Accordingly, communication between the various components of the system 100 may involve multiple network links and different data communication protocols. In this regard, the network can include or cooperate with any of the following, without limitation: a local area network; a wide area network; the Internet; a personal area network; a cellular communication network; a satellite communication network; a video services or television broadcasting network; a network onboard a vehicle; or the like. The components of the system 100 may be suitably configured to support a variety of wireless and wired data communication protocols, technologies, and techniques as needed for compatibility with the network.

In accordance with certain exemplary embodiments, the remote computing device 102 is implemented as at least one computer-based or processor-based component. For simplicity and ease of illustration, FIG. 1 depicts the computing device 102 as a single block—it should be appreciated that any number of distinct hardware components can be utilized to implement the computing device 102. An exemplary embodiment of a device suitable for implementing the computing device 102 is described below with reference to FIG. 2.

For this particular embodiment, the remote computing device 102 can be considered the "heart" of the insulin infusion and management system 100. The computing device 102 includes or cooperates with a database system 116 (which is realized using one or more components) that supports the functionality and operation of the system 100. The remote computing device 102 collects and analyzes input data for each patient (the input data can originate from various sources, including an insulin infusion device and/or a source other than the insulin infusion device, such as: a glucose sensor or meter, a mobile device operated by a user of the insulin infusion device, a computing device, etc.), generates relevant and timely recommendations as needed, and manages the delivery of the generated recommendations to the patient and/or directly to the insulin infusion device 104.

In certain embodiments, some or all of the functionality and processing intelligence of the remote computing device 102 can reside at the insulin infusion device 104 and/or at other components or computing devices that are compatible with the system 100. In other words, the system 100 need not rely on a network-based or a cloud-based server arrangement (as shown in FIG. 1), although such a deployment might be the most efficient and economical implementation. These and other alternative arrangements are contemplated by this disclosure. To this end, some embodiments of the system 100 may include additional devices and components that serve as data sources, data processing units, and/or recommendation delivery mechanisms. For example, the system 100 may include any or all of the following elements, without limitation: computer devices or systems; patient monitors; healthcare provider systems; data communication devices; and the like.

In certain embodiments, the insulin infusion device 104 is a portable patient-worn or patient-carried component that is operated to deliver insulin into the body of the patient via, for example, the infusion set 108. In accordance with certain exemplary embodiments, each insulin infusion device 104 supported by the system 100 is implemented as a computer-based or processor-based component. For simplicity and ease of illustration, FIG. 1 depicts only one insulin infusion device 104. In practice, however, the system 100 is suitably configured to support a plurality of insulin infusion devices 104, wherein each patient or user owns or operates at least one of the insulin infusion devices 104. An exemplary embodiment of a device suitable for implementing the insulin infusion device 104 is described below with reference to FIG. 2.

The system 100 obtains input data from one or more sources, which may include various diabetes management devices (the insulin infusion device 104, a continuous glucose monitoring device, the glucose sensor 106, a monitor device, or the like). In this regard, the insulin infusion device 104 represents a source of input data for the system 100. In certain embodiments, the insulin infusion device 104 provides data that is associated with its operation, status, insulin delivery events, and the like. As mentioned previously, relevant data generated or collected by the insulin infusion device 104 can be transmitted directly to the remote computing device 102 or indirectly by way of the data uploader component 112, depending on the particular implementation of the system 100. The particular type of data provided by the insulin infusion device 104 is described in more detail below.

For the sake of simplicity, FIG. 1 depicts only one glucose sensor 106. In practice, however, the system 100 is suitably configured to support a plurality of glucose sensors 106, wherein each patient or user owns or operates at least one of the glucose sensors 106. The glucose sensor 106 is suitably configured to measure a glucose level (interstitial) of the patient in real time. The glucose sensor 106 may include a wireless transmitter that facilitates transmission of the sensor glucose data to other devices, such as the insulin infusion device 104 or the data uploader component 112. In some implementations, the glucose sensor 106 can provide the sensor glucose data directly to the remote computing device 102 if so desired.

Depending on the particular embodiment and application, the system 100 can include or cooperate with other devices, systems, and sources of input data. For example, in certain embodiments the system 100 includes one or more sources of contextual information or data, which may include, without limitation: activity tracker devices; meal logging devices or apps; mood tracking devices or apps; and the like.

Figure 2:
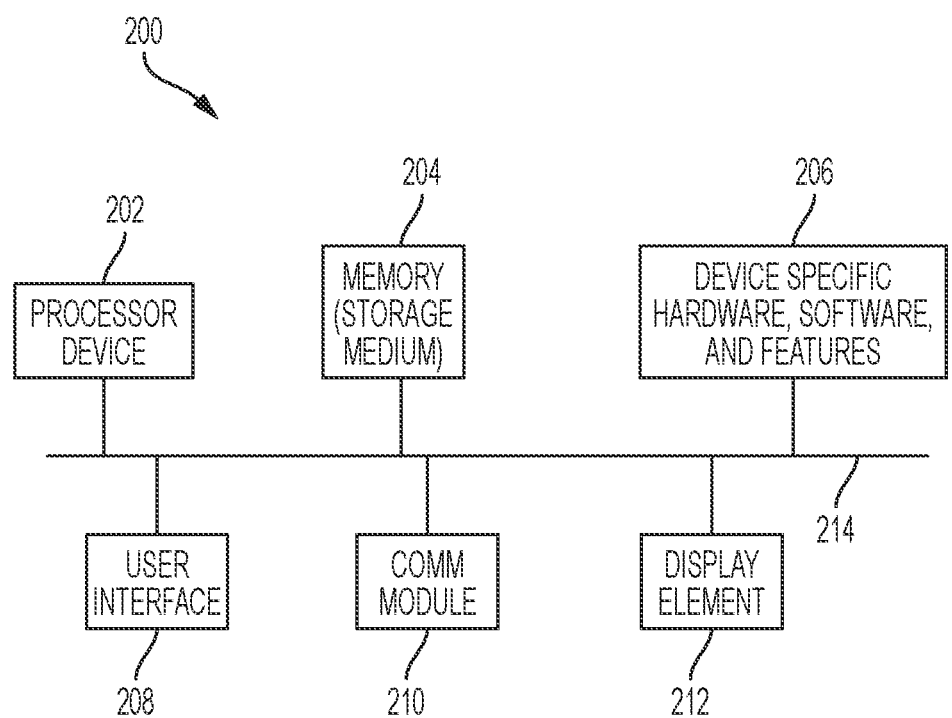
FIG. 2 is a simplified block diagram representation of an exemplary embodiment of a computer-based or processor-based device suitable for deployment in the system shown in FIG. 1.

As mentioned above, the system 100 includes or cooperates with computer-based and/or processor-based components having suitably configured hardware and software written to perform the functions and methods needed to support the features described herein. For example, the remote computing device 102 and each insulin infusion device 104 can be realized as an electronic processor-based component. Moreover, each data uploader component 112 can also be realized as a processor-based component. In this regard, FIG. 2 is a simplified block diagram representation of an exemplary embodiment of a computer-based or processor-based device 200 that is suitable for deployment in the system shown in FIG. 1.

The illustrated embodiment of the device 200 is intended to be a high-level and generic representation of one suitable platform. In this regard, any of the computer-based or processor-based components of the system 100 can utilize the architecture of the device 200. The illustrated embodiment of the device 200 generally includes, without limitation: at least one processor device 202; a suitable amount of memory 204; device-specific hardware, software, firmware, and/or features 206; a user interface 208; a communication module 210; and a display element 212. Of course, an implementation of the device 200 may include additional elements, components, modules, and functionality configured to support various features that are unrelated to the subject matter described here. For example, the device 200 may include certain features and elements to support conventional functions that might be related to the particular implementation and deployment of the device 200. In practice, the elements of the device 200 may be coupled together via a bus or any suitable interconnection architecture 214.

The processor device 202 may be implemented or performed with a general purpose processor, a content addressable memory, a digital signal processor, an application specific integrated circuit, a field programmable gate array, any suitable programmable logic device, discrete gate or transistor logic, discrete hardware components, or any combination designed to perform the functions described here. Moreover, the processor device 202 may be implemented as a combination of computing devices, e.g., a combination of a digital signal processor and a microprocessor, a plurality of microprocessors, one or more microprocessors in conjunction with a digital signal processor core, or any other such configuration.

The memory 204 may be realized as RAM memory, flash memory, EPROM memory, EEPROM memory, registers, a hard disk, a removable disk, a CD-ROM, or any other form of storage medium known in the art. In this regard, the memory 204 can be coupled to the processor device 202 such that the processor device 202 can read information from, and write information to, the memory 204. In the alternative, the memory 204 may be integral to the processor device 202. As an example, the processor device 202 and the memory 204 may reside in an ASIC. At least a portion of the memory 204 can be realized as a computer storage medium that is operatively associated with the processor device 202, e.g., a tangible computer-readable medium having computer-executable instructions stored thereon. The computer-executable instructions, when read and executed by the processor device 202, cause the device 200 to perform certain tasks, operations, functions, and processes that are specific to the particular embodiment. In this regard, the memory 204 may represent one suitable implementation of such computer-readable media. Alternatively or additionally, the device 200 could receive and cooperate with computer-readable media (not separately shown) that is realized as a portable or mobile component or platform, e.g., a portable hard drive, a USB flash drive, an optical disc, or the like.

The device-specific hardware, software, firmware, and features 206 may vary from one embodiment of the device 200 to another. For example, the device-specific hardware, software, firmware, and features 206 will support: insulin pump operations when the device 200 is realized as an insulin infusion device; server system operations when the device 200 is realized as a cloud-based computing device; etc. In practice, certain portions or aspects of the device-specific hardware, software, firmware, and features 206 may be implemented in one or more of the other blocks depicted in FIG. 2.

The user interface 208 may include or cooperate with various features to allow a user to interact with the device 200. Accordingly, the user interface 208 may include various human-to-machine interfaces, e.g., a keypad, keys, a keyboard, buttons, switches, knobs, a touchpad, a joystick, a pointing device, a virtual writing tablet, a touch screen, a microphone, or any device, component, or function that enables the user to select options, input information, or otherwise control the operation of the device 200. The user interface 208 may include one or more graphical user interface (GUI) control elements that enable a user to manipulate or otherwise interact with an application via the display element 212.

The communication module 210 facilitates data communication between the device 200 and other components as needed during the operation of the device 200. In the context of this description, the communication module 210 can be employed to transmit or stream device-related control data, patient-related data, device-related status or operational data, therapy recommendations, infusion device adjustment recommendations and related control instructions, and the like. It should be appreciated that the particular configuration and functionality of the communication module 210 can vary depending on the hardware platform and specific implementation of the device 200. Accordingly, with reference to FIG. 1, the communication module of the remote computing device 102 is utilized to obtain input data from various sources, and to send recommendations and notifications to the insulin infusion device 104. Moreover, the communication module of the insulin infusion device 104 can be used to receive sensor glucose data from the glucose sensor 106, and to send input data to the computing device 102. In practice, an embodiment of the device 200 may support wireless data communication and/or wired data communication, using various data communication protocols. For example, the communication module 210 could support one or more wireless data communication protocols, techniques, or methodologies, including, without limitation: RF; IrDA (infrared); Bluetooth; ZigBee (and other variants of the IEEE 802.15 protocol); IEEE 802.11 (any variation); IEEE 802.16 (WiMAX or any other variation); Direct Sequence Spread Spectrum; Frequency Hopping Spread Spectrum; cellular/wireless/cordless telecommunication protocols; wireless home network communication protocols; paging network protocols; magnetic induction; satellite data communication protocols; wireless hospital or health care facility network protocols such as those operating in the WMTS bands; GPRS; and proprietary wireless data communication protocols such as variants of Wireless USB. Moreover, the communication module 210 could support one or more wired/cabled data communication protocols, including, without limitation: Ethernet; powerline; home network communication protocols; USB; IEEE 1394 (Firewire); hospital network communication protocols; and proprietary data communication protocols.

The display element 212 is suitably configured to enable the device 200 to render and display various screens, recommendation messages, notifications, GUIs, GUI control elements, drop down menus, auto-fill fields, text entry fields, message fields, or the like. Of course, the display element 212 may also be utilized for the display of other information during the operation of the device 200, as is well understood. Notably, the specific configuration, operating characteristics, size, resolution, and functionality of the display element 212 can vary depending upon the practical implementation of the device 200.

The disclosed subject matter relates to a method of managing use of a dual-mode insulin infusion device that is capable of operating in a manual insulin delivery mode or in an automated closed-loop insulin delivery mode. For example, the manual insulin delivery mode can be activated during waking hours, and the closed-loop mode can be activated during sleeping hours. When operating in the manual insulin delivery mode, the infusion device utilizes applicable manual mode settings that influence the manner in which insulin is delivered to the patient. Similarly, when operating in the closed-loop mode, the infusion device utilizes applicable closed-loop settings that influence the manner in which insulin is delivered to the patient. In this regard, a manual-mode basal rate setting can be utilized during operation in the manual insulin delivery mode to regulate the delivery of basal insulin to the patient, and a closed-loop basal rate setting can be utilized during operation in the closed-loop insulin delivery mode to regulate delivery of basal insulin to the patient. Although this description focuses on the adjustment of the basal rate settings, the concepts and methodology presented here can also be utilized to adjust other patient-specific settings of the insulin infusion device, including, without limitation: the insulin sensitivity factor (ISF) of the patient and/or the insulin-to-carbohydrate ratio (carb ratio) of the patient.

In accordance with certain embodiments, the insulin infusion device is suitably configured to automatically adjust basal insulin delivery to maintain glucose within the euglycemic range. The infusion device has two independent operating modes: (i) manual mode where basal insulin is delivered according to a pre-programmed rate or a time-based rate profile; and (ii) closed-loop mode where basal insulin delivery is automatically adjusted (e.g., every five minutes) based on sensor glucose measurements. After a few days of operation in the closed-loop mode, the total daily basal insulin delivered tends to reach a more optimal level due to the constant adjustment of insulin delivery by the feedback controller. The pre-programmed basal rates used for manual mode therapy, usually set at the beginning of insulin infusion device therapy, may not be relevant after a few weeks of therapy in the closed-loop mode due to a variety of reasons. Therefore, it is worthwhile to consider readjusting the manual mode infusion device settings based on the closed-loop insulin delivery profile obtained from data collected from the insulin infusion device.

The following methodology can be taken to recalculate the patient's basal rate based on data obtained from the insulin infusion device. First, obtain a report or analysis of the last N days of pump data, during which the automated closed-loop insulin delivery mode was active (N can be any practical number, such as 7, 14, or the like). Next, obtain at least the total daily dose of insulin (per day) and the total basal insulin delivered (per day) for the patient. A single daily basal rate can be calculated from the obtained data as follows:

$$\text{Basal Rate} \left(\frac{\text{Units}}{\text{Hour}}\right) = \frac{\text{Total Daily Basal Insulin Delivered (Units)}}{24 (\text{Hour})}$$

Multiple daily basal rates can also be calculated based on the distribution of closed-loop mode basal insulin delivery for each designated time segment of the day (e.g., three-hour segments, four-hour segments, one-hour segments). For example, data from 527 patients using a dual-mode insulin infusion device was used to derive the distribution of basal insulin delivered by infusion devices during the automated closed-loop mode for every three-hour segment, as indicated in Table 1 below. Table 1 indicates the average distribution of closed-loop basal insulin delivered for each three-hour segment, based on data collected for the 527 patients using the same type/model of insulin infusion device.

TABLE 1

| Segment No. | Hour of the Day | Average Percentage of Basal Insulin Delivered |
|---|---|---|
| 1 | 0000-0300 | 14.0% |
| 2 | 0300-0600 | 12.7% |
| 3 | 0600-0900 | 12.6% |
| 4 | 0900-1200 | 12.6% |
| 5 | 1200-1500 | 11.7% |
| 6 | 1500-1800 | 12.2% |
| 7 | 1800-2100 | 10.9% |
| 8 | 2100-2400 | 13.3% |

Using population-based data (such as that shown in Table 1), the basal rate per segment of the day can be calculated as follows:

$$\text{Basal Rate Per Segment} = \frac{\text{Average \% Delivered}/100 \times \text{Total Daily Basal Insulin Delivered (Units)}}{3(\text{Hours})}$$

The basal rate per segment of the day (three-hour segment) can also be calculated for various population cohorts, e.g., patients segregated based on gender, demographics, age, insulin requirements, body mass index, disease history, etc. The collected patient and infusion device data can be leveraged to segregate such cohorts based on available information.

The basal rate per segment of the day (three-hour segment) can also be calculated based on only one patient's three-hourly automated closed-loop basal insulin distribution (rather than the population based distribution as shown in the above Table 1). An example for only one patient is provided below. Table 2 below indicates the percentage of closed-loop basal delivered per three-hour segment of the day for this particular user.

TABLE 2

| Segment No. | Hour of the Day | Average Percentage of Basal Insulin Delivered |
|---|---|---|
| 1 | 0000-0300 | 21.9% |
| 2 | 0300-0600 | 15.2% |
| 3 | 0600-0900 | 14.9% |
| 4 | 0900-1200 | 5.5% |
| 5 | 1200-1500 | 9.5% |
| 6 | 1500-1800 | 10.8% |
| 7 | 1800-2100 | 8.8% |
| 8 | 2100-2400 | 13.4% |

The average total basal insulin delivered for the last seven days under the automated closed-loop mode was 19.6 Units for this patient. Therefore, the three-hourly basal rate based on this data can be calculated as shown below in Table 3.

TABLE 3

| Segment No. | Hour of the Day | Three-Hourly Basal Rate Calculations | Basal Rates Per Segment (U/Hour) |
|---|---|---|---|
| 1 | 0000-0300 | = 19.6 × 0.219 | 1.42 |
| 2 | 0300-0600 | = 19.6 × 0.152 | 0.99 |
| 3 | 0600-0900 | = 19.6 × 0.149 | 0.97 |
| 4 | 0900-1200 | = 19.6 × 0.055 | 0.36 |
| 5 | 1200-1500 | = 19.6 × 0.095 | 0.62 |
| 6 | 1500-1800 | = 19.6 × 0.108 | 0.70 |
| 7 | 1800-2100 | = 19.6 × 0.088 | 0.58 |
| 8 | 2100-2400 | = 19.6 × 0.134 | 0.88 |

Instead of three-hourly segments, the day could be divided into four six-hour segments, two twelve-hour segments, or into any number of segments as desired.

In certain embodiments, the infusion device and/or patient data also indicates the average total daily dose (TDD), which is expressed in Units/day. This information can be used to update the patient's insulin sensitivity factor (ISF), which is expressed in mg/dL/Unit. For the exemplary embodiment presented here, the ISF is calculated in accordance with the following equation:

$$ISF = \frac{1800}{\text{Average } TDD}.$$

It should be appreciated that this relationship is merely one example of how the ISF can be calculated. In practice, the methodology and systems described here can calculate the ISF using other formulas or equations if so desired. In this regard, the numerator in the equation need not be 1800 in all cases (values of 1500, 1700, 2000, etc. are also viable). Moreover, although the average TDD value is appropriate here, other statistical representations, measurements, or weighted values may also be utilized. For example, a median TDD value calculated from a defined number of days can be used instead of the average TDD value. As another example, a statistical value (e.g., an average) of the daily auto-bolus amount can be used instead of a TDD based value. These and other variations are contemplated by this disclosure.

Using the methodologies presented here, certain patient-specific settings that influence the operation of the insulin infusion device in the manual delivery mode are adjusted based on an analysis of device/patient data collected while the infusion device is functioning in the automated closed-loop delivery mode. More specifically, the manual-mode basal rate setting and/or the insulin sensitivity factor can be automatically adjusted by the infusion device as needed. Accordingly, the basal rate setting for the manual delivery mode can be adjusted (automatically by the insulin infusion device or otherwise) in an ongoing manner to achieve a better glycemic outcome for the patient. In practice, the patient's open-loop (manual mode) sensor glucose profile should improve over time as a result of this methodology.

Figure 3:
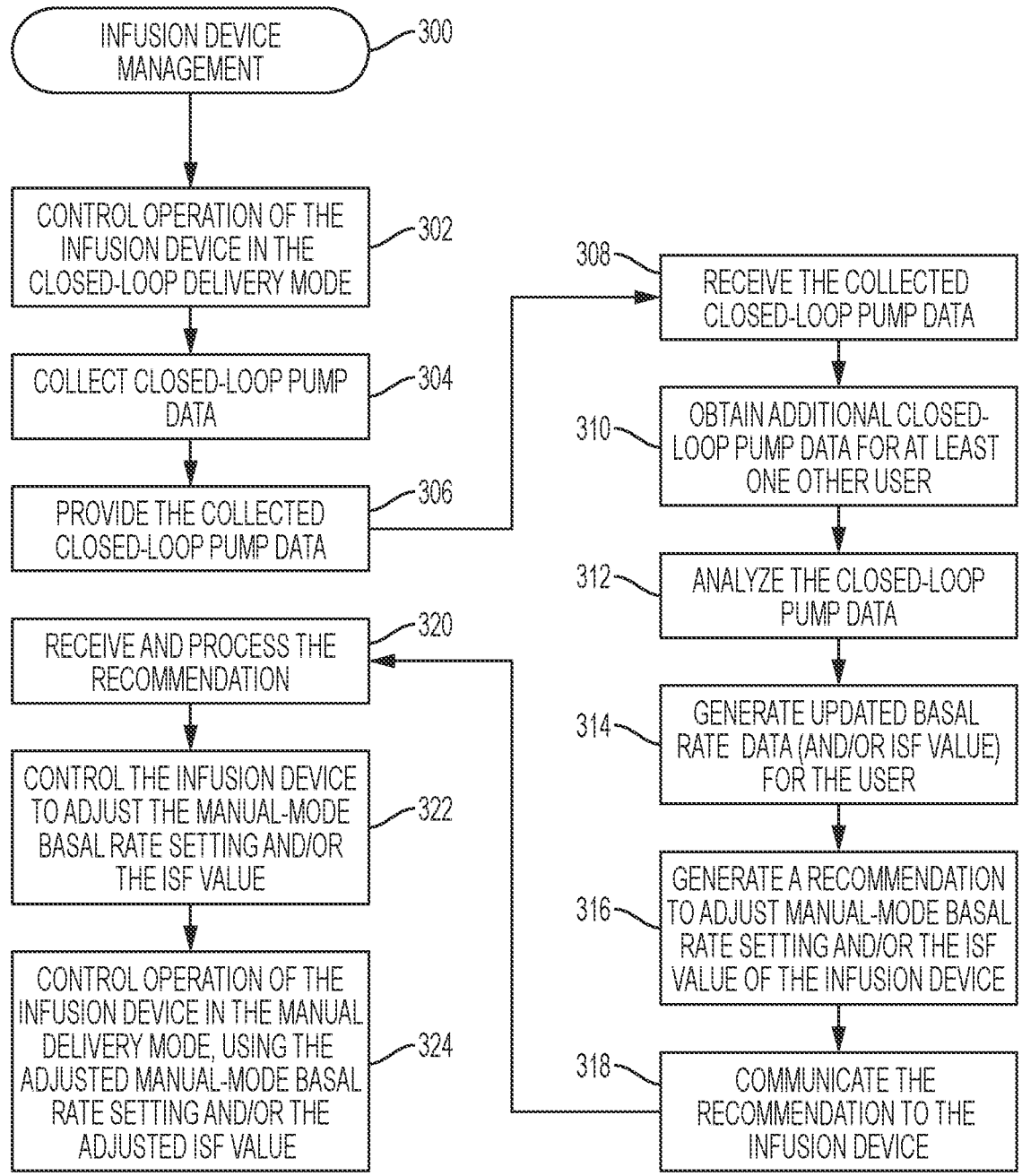
FIG. 3 is a flow chart that illustrates an exemplary embodiment of an infusion device management process.

In this regard, FIG. 3 is a flow chart that illustrates an exemplary embodiment of an infusion device management process 300. The various tasks performed in connection with the process 300 may be performed by software, hardware, firmware, or any combination thereof. For illustrative purposes, the following description of the process 300 may refer to elements mentioned above in connection with FIG. 1 and FIG. 2. In practice, portions of the process 300 may be performed by different elements of the described system, e.g., an infusion device, a data uploader component, a cloud-based computing device, a patient monitor device, a smartphone, a personal computer, or the like. It should be appreciated that the process 300 may include any number of additional or alternative tasks, the tasks shown in FIG. 3 need not be performed in the illustrated order, and the process 300 may be incorporated into a more comprehensive procedure or process having additional functionality not described in detail herein. Moreover, one or more of the tasks shown in FIG. 3 could be omitted from an embodiment of the process 300 as long as the intended overall functionality remains intact.

In practice, the system 100 can be configured to collect and analyze data for multiple patients. Indeed, a centralized cloud-based deployment of the system 100 allows it to be scalable to accommodate a large number of patients. Thus, the techniques and methodologies described herein can be utilized to generate, deliver, and handle recommendations and related infusion device adjustments for different patients. For the sake of brevity and simplicity, the process 300 is described with reference to only one user/patient. It should be appreciated that an embodiment of the system 100 can expand the process 300 in a way that accommodates a plurality of different users/patients.

Although not required, the embodiment of the process 300 includes some tasks performed by the insulin infusion device, and other tasks performed by another computing device (e.g., a cloud-based device, a personal computer owned or operated by the patient, a mobile device owned or operated by the patient, a piece of medical equipment, a data uploader component, or the like). The following description assumes that the patient's insulin infusion device 104 performs certain tasks, and that the remote computing device 102 performs other tasks (see FIG. 1). To this end, the blocks on the left side of FIG. 3 represent tasks performed by the insulin infusion device 104, and the blocks on the right side of FIG. 3 represent tasks performed by the remote computing device 102.

As explained above, the process 300 represents an exemplary embodiment of a method of managing use of a dual-mode insulin infusion device that operates in a manual insulin delivery mode or an automated closed-loop insulin delivery mode. This example assumes that the insulin infusion device is controlled to operate in the closed-loop delivery mode (task 302). Operation in the closed-loop delivery mode can be initiated by: the patient; a caregiver; automatically by the insulin infusion device; remotely by a device, system, or component that communicates with the insulin infusion device; etc. In practice, the controller/processor of the insulin infusion device is responsible for controlling operation in the closed-loop mode.

While the insulin infusion device is operating in the closed-loop delivery mode, the process 300 collects closed-loop pump data for the user of the infusion device (task 304). The closed-loop pump data includes data related to the status of the infusion device and/or the status of the user. The closed-loop pump data includes, without limitation, data indicating basal insulin delivered by the insulin infusion device to the user during operation in the automated closed-loop insulin delivery mode for at least one defined period of time (e.g., an eight-hour period, a number of sequential one-hour periods, or a number of sequential three-hour periods). In certain embodiments, the closed-loop pump data also includes data that indicates the total amount of insulin delivered by the infusion device during at least one defined period of time (e.g., the last 24 hours, a number of sequential segments of time, etc.), such as the average total daily dose (TDD) of insulin for the user. The closed-loop pump data may also include glucose sensor data, log data for the infusion device, user-input data, time/calendar data associated with certain events or collected data, and/or other information that is not particularly relevant to the subject matter described here.

The closed-loop pump data can be collected and stored in memory that resides at the insulin infusion device. Eventually, the collected closed-loop pump data is provided to at least one computing device for analysis and handling (task 306). This example assumes that the insulin infusion device communicates the collected closed-loop pump data to the remote computing device, directly or via one or more intermediary components, such as the data uploader component 112 shown in FIG. 1. The pump data can be automatically uploaded after the infusion device exits the closed-loop mode, or uploading can be initiated by the user, a caregiver, etc.

This description assumes that the collected closed-loop pump data is successfully received by the remote computing device (task 308). The received pump data originates from the insulin infusion device of one user/patient. The remote computing device, however, can be designed and programmed to support a plurality of different users and a plurality of different insulin infusion devices, which in turn generate and provide corresponding pump data. Accordingly, the process 300 can (optionally) obtain additional closed-loop pump data for at least one other user (task 310), wherein the additional pump data originates from respective insulin infusion devices. Task 310 is optional because the methodology described here can receive and analyze the pump data for any one individual patient, or for two or more patients, wherein the resulting adjustment recommendations for the given patient are based on the patient-specific pump data by itself or based on the pump data collected from multiple patients.

The process 300 continues by analyzing the received closed-loop pump data (task 312). As mentioned above, the pump data to be analyzed may be specific to the given patient, or it may be associated with a plurality of different patients. The received closed-loop pump data is reviewed and analyzed to generate updated basal rate data for the particular user (task 314). Thus, the updated basal rate data can be generated based only on the pump data for that particular user, based on the pump data for that particular user and pump data for at least one other user, or based on the pump data for at least one other user (without considering the pump data for the particular user). In certain embodiments, task 312 considers the total amount of insulin delivered in the automated closed-loop delivery mode for a specific period of time, and that amount becomes the basal rate for that period of time. Assume, for example, that over the last two weeks an average of 3.0 Units of insulin was delivered to the patient during closed-loop operation between the hours of 3:00 AM and 6:00 AM. The new basal rate (to be used in the manual mode) for the time segment between 3:00 AM and 6:00 AM will be 1.0 Unit/Hour. As another example, if the closed-loop mode delivered an average of 36 Units of basal insulin per day for the last two weeks, then the updated basal rate will be 1.5 Unit/Hour.

The process 300 can also update the ISF value of the user, based on TDD information included with the closed-loop pump data (task 314). As mentioned above, the ISF can be calculated as follows:

$$ISF = \frac{X}{\text{Average } TDD},$$

where the value of X may be (for example) 1800, 1500, 2000, or the like. In practice, the process 300 can update the basal rate by itself, the ISF value by itself, or both the basal rate and the ISF value.

This description assumes that the updated basal rate and/or the updated ISF value are different than their current values by at least a threshold amount, such that the current values should be adjusted. Accordingly, the process 300 continues by generating (from the updated basal rate data and/or from the updated ISF value) a recommendation to adjust certain settings of the insulin infusion device (task 316). To this end, the remote computing device generates a recommendation to adjust the manual-mode basal rate setting of the insulin infusion device and/or a recommendation to adjust the ISF value of the insulin infusion device. The recommendation can be arranged, formatted, and otherwise configured in an appropriate manner for presentation or communication to the user. In this regard, the recommendation can be provided in (or implemented as) a user readable format, such as an email, a text message, an HTML, document (web page), a displayable report, or the like. Alternatively (or additionally), the recommendation can be realized as any computer-readable data object, metadata, a control/command signals or instructions, or the like. The recommendation may be intended for immediate presentation via the computing device that generates the recommendation, or intended for presentation via a linked or associated destination device or system, such as the insulin infusion device, a patient monitor device, or the patient's smartphone device. In accordance with the exemplary embodiment described here, the recommendation is configured and formatted for presentation at the insulin infusion device, and it includes certain commands or control instructions that can be executed by the insulin infusion device to make recommended adjustments to one or more settings of the device.

In accordance with the illustrated embodiment of the process 300, the recommendation is communicated from the originating computing device to the insulin infusion device (task 318). This example assumes that the recommendation (or whatever data is utilized to convey the recommendation) is successfully received and processed by the insulin infusion device (task 320). In response to receiving and processing the recommendation, the insulin infusion device takes appropriate action. For example, the infusion device can display, announce, or otherwise present the substance of the recommendation to the patient, using the native capabilities of the infusion device. As another example, the infusion device can be suitably configured to automatically adjust certain settings, as indicated in the recommendation. As yet another example, in response to receiving and processing the recommendation, the infusion device can be prepared to adjust certain settings after receiving a confirmation or authorization from the patient, a caregiver, or other user.

The exemplary embodiment of the process 300 automatically controls the insulin infusion device to adjust the manual-mode basal rate setting in accordance with the parameters or values conveyed in the recommendation (task 322). Alternatively or additionally, the process 300 automatically controls the insulin infusion device to adjust the ISF in accordance with the updated ISF value conveyed in the recommendation (task 322). In this regard, the relevant settings of the insulin infusion device can be automatically updated by way of a recommendation generated by the remote computing device. Eventually, the insulin infusion device is controlled to operate in the manual insulin delivery mode (task 324). Operation in the "post-adjustment" manual mode may occur automatically and seamlessly without further user/patient involvement, or the recent adjustments may become effective upon entry of the next manual delivery mode. During operation in the manual insulin delivery mode, the insulin infusion device implements and uses the manual-mode basal rate setting (as adjusted) and/or the adjusted ISF value, which were conveyed in the recommendation obtained from the remote computing device.

The patient's carb ratio can be adjusted in a similar manner. In this regard, one classical relationship for carb ratio is expressed as $$CR = \frac{Y}{TDD},$$

where Y is a suitably chosen or calculated value, such as 500. Consequently, the carb ratio can be handled as described above for the ISF value (due to the similarity in their defining relationships). It should be appreciated that the carb ratio value may also be calculated using a statistical value that is based on the patient's daily auto-bolus amount. These and other techniques for adjusting the carb ratio are contemplated by this disclosure.

An iteration of the process 300 can be repeated as needed or required. For example, the process 300 can be performed following each period of closed-loop operation. Alternatively, an iteration of the process 300 can be performed following any designated number of closed-loop periods, using pump data collected during each period of closed-loop operation. As another example, the process 300 can be performed weekly, monthly, daily, or the like.

In accordance with certain implementations, the manual-mode basal rate setting includes or represents a basal rate profile that defines a plurality of manual-mode basal rates corresponding to a plurality of time segments of a 24-hour day, and at least some of the manual-mode basal rates are adjusted in accordance with the recommendation. For example, as described above with reference to Table 3, a 24-hour period can be divided into eight three-hour segments, each having a respective basal rate. For such a scenario, any or all of the eight basal rates can be adjusted using the methodology described here. In accordance with another implementation, the manual-mode basal rate setting includes or represents a single basal rate value for a 24-hour period, and that particular basal rate value is adjusted in accordance with the recommendation. These and other variations are contemplated by this disclosure.

The exemplary embodiment of the process 300 described above leverages the processing intelligence, resources, and power of a cloud-based system. In accordance with an alternative embodiment, however, the insulin infusion device itself can analyze the pump data, generate the recommendation, and act upon the recommendation as needed. In other words, the methodology described here can be realized in the context of a stand-alone insulin infusion device, without any remote processing component. To this end, the insulin infusion device can analyze its collected pump data at an appropriate time, generate recommendations, and self-implement or self-execute the recommendations as needed. As mentioned previously, the infusion device can automatically enter the recommended adjustments, or it can wait to receive a confirmation or approval (from the patient, a caregiver, or other authorized user) before entering the recommended adjustments.

The example described above communicates the recommendation from the remote cloud-based computing device to the insulin infusion device, which takes appropriate action in response to receiving the recommendation. In accordance with alternative embodiments, however, the recommendation need not be delivered to the insulin infusion device. Instead, the recommendation can be provided, communicated, or otherwise delivered to a device, system, or component other than the insulin infusion device. The destination device may be, for example: a laptop computer, desktop computer, or tablet computer; a mobile device such as a smartphone; a wearable computing device; medical equipment or a medical device other than the insulin infusion device; a video game device; a home entertainment device or system; a computer-based smart appliance; or any suitably configured and programmed computer-based device. For such embodiments, the destination device can serve as an intermediary or interface device to forward the recommendation to the insulin infusion device, or it can serve as a "notification" device that presents the recommendation to a user, who in turn must take appropriate action (e.g., make the recommended adjustments to the infusion device settings, control the infusion device in an appropriate manner, authorize the automated update of the infusion device settings, or the like).

While at least one exemplary embodiment has been presented in the foregoing detailed description, it should be appreciated that a vast number of variations exist. It should also be appreciated that the exemplary embodiment or embodiments described herein are not intended to limit the scope, applicability, or configuration of the claimed subject matter in any way. Rather, the foregoing detailed description will provide those skilled in the art with a convenient road map for implementing the described embodiment or embodiments. It should be understood that various changes can be made in the function and arrangement of elements without departing from the scope defined by the claims, which includes known equivalents and foreseeable equivalents at the time of filing this patent application.

What is claimed is:

1. A processor-implemented method comprising:
   accessing insulin delivery data for a user of an insulin delivery device, wherein the insulin delivery data was collected during a closed-loop mode of the insulin delivery device and is indicative of a total amount of insulin delivered by the insulin delivery device to the user during a time period;
   generating an updated insulin sensitivity factor (ISF) value based on an average total daily dose (TDD) of insulin determined using the insulin delivery data collected during the closed-loop mode;
   generating, based on the updated ISF value, a recommendation to adjust an ISF value for a manual mode of the insulin delivery device, wherein the ISF value for the manual mode is separate from an ISF value for the closed-loop mode; and
   causing the insulin delivery device to deliver insulin in the manual mode based on the updated ISF value in accordance with the recommendation.

2. The processor-implemented method of claim 1, wherein the processor-implemented method is performed by a computing device in data communication with the insulin delivery device.

3. The processor-implemented method of claim 1, further comprising communicating the recommendation to the insulin delivery device to adjust the ISF value on the insulin delivery device.

4. The processor-implemented method of claim 1, further comprising controlling operation of the insulin delivery device in accordance with the updated ISF value.

5. The processor-implemented method of claim 1, wherein the total amount of insulin delivered to the user during the time period comprises the average total daily dose (TDD) of insulin for the user.

6. The processor-implemented method of claim 1, wherein:
   the ISF value is updated in accordance with an expression $$ISF = \frac{X}{\text{Average } TDD};$$

ISF is expressed in units of mg/dL/Unit;
   X is expressed in units of mg/dL/day and relates to an insulin regimen of the insulin delivery device; and
   Average TDD is expressed in units of Units/day.

7. The processor-implemented method of claim 1, wherein the processor-implemented method is performed by the insulin delivery device.

8. The processor-implemented method of claim 1, wherein generating the recommendation includes generating, based on the updated ISF value being different from a current ISF value by at least a threshold amount, the recommendation to adjust the ISF value for the manual mode of the insulin delivery device.

9. A system comprising:
   one or more processors; and
   one or more processor-readable storage media operatively coupled with the one or more processors, the one or more processor-readable storage media storing executable instructions which, when executed by the one or more processors, cause performance of operations comprising:
      accessing insulin delivery data for a user of an insulin delivery device, wherein the insulin delivery data was collected during a closed-loop mode of the insulin delivery device and is indicative of a total amount of insulin delivered by the insulin delivery device to the user during a time period;
      generating, based on an average total daily dose (Average TDD) of insulin determined using the insulin delivery data collected during the closed-loop mode, an updated insulin sensitivity factor (ISF) value in accordance with an expression $$ISF = \frac{X}{\text{Average } TDD};$$

wherein X relates to an insulin regimen of the insulin delivery device;
      generating, based on the updated ISF value, a recommendation to adjust an ISF value for a manual mode of the insulin delivery device, wherein the ISF value for the manual mode is separate from an ISF value for the closed-loop mode; and
      causing the insulin delivery device to deliver insulin in the manual mode based on the updated ISF value in accordance with the recommendation.

10. The system of claim 9, wherein the operations are performed by a computing device in data communication with the insulin delivery device, and wherein the computing device comprises the one or more processors and the one or more processor-readable storage media.

11. The system of claim 9, wherein the operations further comprise communicating the recommendation to the insulin delivery device to adjust the ISF value on the insulin delivery device.

12. The system of claim 9, wherein the one or more processor-readable storage media further store instructions which, when executed by the one or more processors, cause performance of: controlling operation of the insulin delivery device in accordance with the updated ISF value.

13. The system of claim 9, wherein the total amount of insulin delivered to the user during the time period comprises the average total daily dose (TDD) of insulin for the user.

14. The system of claim 9, wherein the operations are performed by the insulin delivery device, and wherein the insulin delivery device comprises the one or more processors and the one or more processor-readable storage media.

15. One or more non-transitory processor-readable storage media storing executable instructions which, when executed by one or more processors, cause performance of operations comprising:
 accessing insulin delivery data for a user of an insulin delivery device, wherein the insulin delivery data was collected during a closed-loop mode of the insulin delivery device and is indicative of a total amount of insulin delivered by the insulin delivery device to the user during a time period;
 generating an updated ISF value based on an average total daily dose (TDD) of insulin determined using the insulin delivery data collected during the closed-loop mode;
 generating, based on the updated ISF value, a recommendation to adjust an ISF value for a manual mode of the insulin delivery device, wherein the ISF value for the manual mode is different from an ISF value for the closed-loop mode; and
 causing the insulin delivery device to deliver insulin in the manual mode based on the updated ISF value in accordance with the recommendation.

16. The one or more non-transitory processor-readable storage media of claim 15, wherein the operations are performed by a computing device in data communication with the insulin delivery device.

17. The one or more non-transitory processor-readable storage media of claim 15, wherein the operations further comprise communicating the recommendation to the insulin delivery device to adjust the ISF value on the insulin delivery device.

18. The one or more non-transitory processor-readable storage media of claim 15, wherein the total amount of insulin delivered to the user during the time period comprises the average total daily dose (TDD) of insulin for the user.

19. The one or more non-transitory processor-readable storage media of claim 15, wherein:
 the ISF value is updated in accordance with an expression $$ISF = \frac{X}{\text{Average } TDD};$$

and
 X relates to an insulin regimen of the insulin delivery device.

20. The one or more non-transitory processor-readable storage media of claim 15, wherein the operations are performed by the insulin delivery device.

* * * * *